United States Patent [19]

Demler et al.

[11] 4,350,827

[45] Sep. 21, 1982

[54] METHOD FOR RECOVERING PURE METAHYDROXYBENZOIC ACID

[75] Inventors: Walter R. Demler, Hamburg; Eugene Odin, Williamsville, both of N.Y.

[73] Assignee: Buffalo Color Corporation, West Paterson, N.J.

[21] Appl. No.: 300,196

[22] Filed: Sep. 8, 1981

[51] Int. Cl.³ .............................................. C07C 65/01
[52] U.S. Cl. .................................................... 562/475
[58] Field of Search ......................................... 562/475

[56] References Cited

U.S. PATENT DOCUMENTS 3,468,942  9/1969  Blum ................................... 562/475

FOREIGN PATENT DOCUMENTS

| 11815 | 6/1980 | European Pat. Off. | ............ 562/475 |
|---|---|---|---|
| 45-10489 | 4/1970 | Japan | ................... 562/475 |
| 46-25729 | 7/1971 | Japan | ................... 562/475 |
| 384558 | 12/1932 | United Kingdom | ................ 562/475 |

*Primary Examiner*—Paul J. Killos
*Attorney, Agent, or Firm*—Michael L. Dunn

[57] ABSTRACT

A method for recovering purified m-hydroxybenzoic acid from crude m-hydroxybenzoic acid alkali metal salt. The method comprises dissolving the crude m-hydroxy benzoic acid alkali metal salt in water at a ratio of between about 13 and 20 milliliters of water per gram of pure m-hydroxybenzoic acid alkali metal salt contained in the crude salt; acidifying the resulting solution to a pH of below 2 with a mineral acid to neutralize all alkali metal hydroxide present and to convert the m-hydroxybenzoic acid alkali metal salt to free m-hydroxybenzoic acid; and cooling the solution to from about 0° C. to about 15° C. for a sufficient time to crystallize purified m-hydroxybenzoic acid from the solution.

The method is particularly effective for removing impurities of parahydroxybenzoic acid, alkali metal hydroxide and water soluble inorganic salts.

10 Claims, No Drawings

METHOD FOR RECOVERING PURE METAHYDROXYBENZOIC ACID

BACKGROUND OF THE INVENTION

(A) Field of the Invention

This invention relates to the preparation of metahydroxybenzoic acid (m-hydroxybenzoic acid) by fusion of metasulfobenzoic acid with an alkali metal hydroxide and more particularly relates to a method for recovering m-hydroxybenzoic acid from the fusion reaction mass.

(B) History of the Prior Art

In the prior art, it was known to dilute a reaction fusion mass used to prepare m-hydroxybenzoic acid alkali metal salt followed by acidifying the resulting solution to crystallize m-hydroxybenzoic acid (see e.g., U.S. Pat. No. 3,468,942; U.S. Pat. No. 3,094,558; Kirk-Othmer Volume 17, 2nd Edition, page 736; American Chemical Journal, 1912, page 432 and Justus Liebig's Annalen Der Chemie, Volume 280, 1894, Kekule et al.)

The products resulting from isolation by dissolving the fusion mass for preparation of m-hydroxybenzoic alkali metal salt followed by crystallization of m-hydroxybenzoic acid from the resulting solution by acidification frequently contains substantial quantities of isomers of hydroxybenzoic acid other than the meta isomer. In particular, an undesirably large quantity of parahydroxybenzoic acid is often present. It was therefore frequently necessary to recrystallize the m-hydroxybenzoic acid initially obtained from the dissolved fusion mass in order to obtain a m-hydroxybenzoic acid product of the desired purity. Such recrystallizations frequently result in loss of yield due to the solubility of the m-hydroxybenzoic acid in the crystallization medium.

BRIEF DESCRIPTION OF THE INVENTION

In accordance with the present invention, there is provided a method for recovering purified m-hydroxybenzoic acid from crude m-hydroxybenzoic acid alkali metal salt. The method is particularly effective when the crude m-hydroxybenzoic acid alkali metal salt contains an impurity of parahydroxybenzoic acid, alkali metal hydroxide, water soluble inorganic salts or mixtures of such impurities.

The method of the invention comprises dissolving the crude m-hydroxybenzoic acid alkali metal salt in water at a ratio of between about 13 and 20 milliliters of water per gram of pure m-hydroxybenzoic acid alkali metal salt contained in the crude m-hydroxybenzoic acid alkali metal salt. After the crude m-hydroxybenzoic acid salt is dissolved, the resulting solution is acidified to a pH of below 2 with mineral acid to neutralize all alkali metal hydroxide present and to convert the m-hydroxybenzoic acid salt to free m-hydroxybenzoic acid. The solution during acidifying is maintained at a sufficiently high temperature to prevent crystallization of m-hydroxybenzoic acid from the solution.

After the solution is acidified, it is cooled to and maintained at a temperature of from about 0° C. to about 15° C. for a sufficient time for essentially all m-hydroxybenzoic acid to crystallize from the solution. After the m-hydroxybenzoic acid crystallizes from the solution, it is separated from the solution.

DETAILED DESCRIPTION OF THE INVENTION

"Purified m-hydroxybenzoic acid", as used herein, means m-hydroxybenzoic acid product containing less than 0.5 weight percent parahydroxybenzoic acid and which upon drying, contains less than a total of 1 weight percent impurity. The purified m-hydroxybenzoic acid is recovered from crude m-hydroxybenzoic acid alkali metal salt containing impurities of parahydroxybenzoic acid, alkali metal hydroxide and water soluble inorganic salts. In general, to obtain a product containing less than 0.5 weight percent parahydroxy benzoic acid, in order for the method to be operative, the crude m-hydroxybenzoic acid salt should contain no more than about 6% parahydroxybenzoic acid alkali metal salt by weight of m-hydroxybenzoic acid alkali metal salt. In general, "alkali metal salt", as used herein, means sodium or potassium salts. The crude m-hydroxybenzoic acid alkali metal salt also contains water soluble inorganic salts. The water soluble inorganic salt in general is selected from the group consisting of potassium chloride, sodium chloride, potassium sulfite, sodium sulfite, potassium sulfate, sodium sulfate, potassium bisulfate, potassium bisulfite, sodium bisulfate, sodium bisulfite and mixtures thereof.

In general, the crude m-hydroxybenzoic acid alkali metal salt contains less than 100% combined alkali metal hydroxide and water soluble inorganic salt by weight of m-hydroxybenzoic acid alkali metal salt contained in the crude m-hydroxybenzoic acid alkali metal salt.

The method of the invention comprises dissolving the crude m-hydroxybenzoic acid alkali metal salt in water at a ratio of between about 13 and 20 milliliters and preferably between about 14 and about 17 milliliters of water per gram of pure m-hydroxybenzoic acid alkali metal salt contained in the crude product. The crude product may be dissolved at ambient or elevated temperature (e.g., up to 100° C.) and may be dissolved with or without agitation. This particular ratio of water to m-hydroxybenzoic acid is critical to the operativeness of the invention.

After the crude product is dissolved, the resulting solution is acidified to a pH of below 2 and preferably below about 1 with mineral acid to neutralize all alkali metal hydroxide present and to convert the m-hydroxybenzoic acid alkali metal salt to free m-hydroxybenzoic acid. The mineral acid may be any mineral acid such as an acid selected from the group consisting of HCl, HBr, $H_2SO_4$, $H_2SO_3$ and $HNO_3$. In general, the mineral acid is most desirably HCl. During neutralization, the solution is maintained at a sufficiently high temperature, usually above 70° C. and below 100° C. and preferably between 75° C. and 85° C., to prevent crystallization of m-hydroxybenzoic acid from the solution as the solution is acidified.

After acidification, the solution is cooled to and maintained at a temperature of from about 0° C. to about 15° C. and preferably from about 8° C. to about 12° C. for a sufficient time of from 30 minutes to 24 hours for essentially all m-hydroxybenzoic acid to crystallize from the solution. "Essentially all", as used in this context, means that in excess of about 90% and usually in excess of 95% of the m-hydroxybenzoic acid contained in this solution crystallizes from the solution. This low crystallization temperature in conjunction with the particular water to m-hydroxybenzoic acid ratio is what permits a high yield of m-hydroxybenzoic acid while greatly reducing the presence of parahydroxy benzoic acid.

After essentially all m-hydroxybenzoic acid crystallizes from the solution, it is separated from the solution by any suitable means such as filtration. The crystallized m-hydroxybenzoic acid may also be separated by permitting the m-hydroxybenzoic acid to settle either by gravity or by centrifugal force or both followed by decanting the solution from the crystallized m-hydroxybenzoic acid.

Desirably, the solution is clarified prior to its acidification by any suitable method such as filtration. Such clarification removes any water insoluble substances from the solution.

The method of the invention is a simple method for recovering purified m-hydroxybenzoic acid from the crude product resulting from fusion of m-sulfobenzoic acid with alkali metal hydroxide. The method permits the meta isomer to be separated from substantial quantities of the para isomer which may be simultaneously prepared in the fusion.

The following examples serve to illustrate and not limit the present invention. Unless otherwise indicated, all parts and percentages are by weight.

EXAMPLE 1

865 Grams of sodium hydroxide flakes and 335 grams of 90% KOH flakes were heated to melt at 200° C. to 210° C. At 220° C., 1386 grams of 96.98% monosodium salt of m-sulfobenzoic acid was added over a period of two hours at 220° C. to 250° C. The fusion mass was held for an additional two hours at 240° C. to 250° C. and the syrupy fusion mass was poured out into a stainless steel pan and cooled. 2239 Grams of hardened melt and 3300 milliliters of solution resulting from washing of the pot and pan were obtained.

EXAMPLE 2

To illustrate workup of the fusion mass at a water to m-hydroxybenzoic acid not in accordance with the present invention to obtain separated m-hydroxybenzoic acid, 223.9 grams of the hardened melt from Example 1 and 1/10th of the washed solution from Example 1 (330 milliliters) were added to a 2 liter beaker. The combined melt and washed solution were diluted with 260 milliliters of hot water. About 6 grams of Brown Company's Solka Floc cellulose filter product was added to the solution and stirred. The solution was then sludge filtered through a 1 centimeter thick Solka Floc bed and the bed was washed with two 75 milliliter portions of hot water. The total volume of the solution after washing was 850 milliliters. The solution was heated to about 75° C. and hydrochloric acid was added to a pH of less than 1.0. After the hydrochloric acid was added, the temperature was 83° C. The solution, contained in the 2 liter beaker, was then set in an ice bath and the solution was permitted to cool without agitation to a temperature of from 8° C. to 12° C. until apparent crystallization from the solution stopped. The solution was then filtered and the beaker rinsed with filtrate and the filtrate was then passed through the filter. The resulting wet cake was washed twice with 100 milliliters of ice water and the product was vacuumed dried at 110° C. 78.7 grams of m-hydroxybenzoic acid product was obtained with a melting point of 202° C. to 203° C. The product had no acetone insolubles. Gas chromotography analysis indicated that the product contained over 98% m-hydroxybenzoic acid and over 1.5% parahydroxybenzoic acid. The yield of m-hydroxybenzoic acid was calculated to be about 93% of theoretical.

Analysis of both the dry product and the filtrate indicated that the original crude product contained about 3% parahydroxybenzoic acid based upon the weight of the m-hydroxybenzoic acid.

EXAMPLE 3

Example 2 is repeated except that the melt was diluted with water in the appropriate ratio in accordance with the present invention. In particular, 223.9 grams of the crude fusion mass from Example 1 and 1/10th of the washed solution from Example 1 (330 mls) were added to a 2 liter beaker with 850 milliliters of hot water. The solution was stirred and heated to a temperature of from 75° to 80° C. and about 6 grams of Brown Company's Solka Floc cellulose filter product was added to the solution. The solution was then sludge filtered through a 1 centimeter thick Solka Floc bed and washed with two portions of 75 milliliters of hot water. The volume after washing was 1350 milliliters which was heated in a beaker to 75° C. and hydrochloric acid was added to a pH of less than 1. After the acid was added, the temperature of the solution was 83° C. The beaker containing the solution was then set in an ice bath and let cool without agitation to a temperature of from 8° C. to 12° C. until apparent crystallization stopped. The solution was then filtered. The beaker was rinsed with filtrate which was then also filtered. The wet cake was then washed twice with 100 milliliters of ice water and the product was vacuum dried at 110° C. 74.7 grams of dry product were obtained with a melting point of 203° C. to 204° C. with no acetone insolubles. The product was found by gas chromotography analysis to be almost 100% m-hydroxybenzoic acid which contained less than 0.5% parahydroxybenzoic acid. The yield was calculated to be about 90% of theoretical. A comparison of Examples 2 and 3 clearly shows that the method of the invention using cooling and an appropriate ratios of dissolving water to m-hydroxybenzoic acid alkali metal salt in the fusion of m-sulfobenzoic acid and alkali metal hydroxide to obtain the salt, results in a finished m-hydroxybenzoic acid product having greater purity and containing substantially less p-hydroxybenzoic acid without a large loss in yield.

What is claimed is:

1. A method for recovering purified metahydroxybenzoic acid from crude m-hyroxybenzoic acid alkali metal salt comprising:
   (a) dissolving the crude m-hydroxybenzoic acid alkali metal salt in water at a ratio of between about 13 and 20 milliliters of water per gram of pure m-hydroxybenzoic acid alkali metal salt contained in the crude m-hydroxybenzoic acid alkali metal salt;
   (b) acidifying the resulting solution to a pH of below 2 with mineral acid to neutralize all alkali metal hydroxide present and convert the m-hydroxybenzoic acid alkali metal salt to free m-hydroxybenzoic acid, the solution, during acidifying, being maintained at a sufficiently high temperature to prevent crystallization of m-hydroxybenzoic acid from the solution;
   (c) cooling the solution to and maintaining the solution at from about 0° C. to about 15° C. for a sufficient time for essentially all m-hydroxybenzoic acid to crystallize from the solution; and (d) separating the resulting m-hydroxybenzoic acid crystals from the solution.

2. The method of claim 1 wherein the sufficiently high temperature is above 70° C. and below 100° C.

3. The method of claim 2 wherein the sufficiently high temperature is between 75° C. and 85° C.

4. The method of claim 1 wherein the sufficient time is from 30 minutes to 24 hours.

5. The method of claim 2 wherein the sufficient time is from 30 minutes to 24 hours.

6. The method of claim 1 wherein in step (b), the solution is acidified to a pH of below 1.

7. The method of claim 2 wherein in step (b), the solution is acidified to a pH of below 1.

8. The method of claim 1 wherein in step (c), the solution is cooled and maintained at a temperature of from 8° C. to 12° C.

9. The method of claim 2 wherein in step (c), the solution is cooled and maintained at a temperature of from 8° C. to 12° C.

10. The method of claim 6 wherein in step (c), the solution is cooled and maintained at a temperature of from 8° C. to 12° C.

* * * * *